United States Patent
Marcussen et al.

(10) Patent No.: US 6,700,033 B1
(45) Date of Patent: Mar. 2, 2004

(54) LAYERED PRODUCT READY FOR NON TOUCH APPLICATION AND A METHOD FOR PRODUCING SUCH A PRODUCT

(75) Inventors: Jan Marcussen, Taastrup (DK); Lars Bo Madsen, Gentofte (DK); Grazyna Hansen, Farum (DK)

(73) Assignee: Coloplast A/S, Humlebaek (DK)

(*) Notice: Subject to any disclaimer, the term of this patent is extended or adjusted under 35 U.S.C. 154(b) by 0 days.

(21) Appl. No.: 09/831,902

(22) PCT Filed: Nov. 25, 1999

(86) PCT No.: PCT/DK99/00658

§ 371 (c)(1),
(2), (4) Date: May 25, 2001

(87) PCT Pub. No.: WO00/30580

PCT Pub. Date: Jun. 2, 2000

(30) Foreign Application Priority Data

Nov. 25, 1998 (DK) .................................. 1998 01547

(51) Int. Cl.[7] .................................................. A61F 13/00
(52) U.S. Cl. ........................... 602/57; 602/54; 206/440; 206/441
(58) Field of Search ............................. 602/41, 57, 58, 602/42, 43, 44, 45, 46, 48, 54, 55, 56; 128/888, 889; 206/440, 441; 424/443–449

(56) References Cited

U.S. PATENT DOCUMENTS

| | | | |
|---|---|---|---|
| 4,423,101 A | * 12/1983 | Willstead | 428/76 |
| 5,099,832 A | 3/1992 | Ward | 602/57 |
| 5,106,629 A | 4/1992 | Cartmell et al. | 424/445 |
| 5,333,753 A | * 8/1994 | Etheredge | 221/33 |
| 5,397,297 A | 3/1995 | Hunter | 602/54 |
| 5,685,833 A | * 11/1997 | Turngren | 602/58 |
| 5,840,052 A | 11/1998 | Johns | 602/54 |

FOREIGN PATENT DOCUMENTS

| | | |
|---|---|---|
| EP | 0 330 825 | 9/1989 |
| EP | 0 938 882 | 9/1999 |
| WO | 97/43991 | 11/1997 |
| WO | 98/00080 | 1/1998 |

* cited by examiner

*Primary Examiner*—Kim M. Lewis
(74) *Attorney, Agent, or Firm*—Jacobson Holman PLLC

(57) ABSTRACT

A layered product in a package ready for non-touch application which product comprises a cover layer to which an adhesive layer is unreleasably fastened and a release layer which is releasably fastened to the adhesive layer, and which package comprises a top layer and a bottom layer where the top layer is next to the cover layer and the bottom layer is next to the adhesive layer or the release layer and the top and bottom layer are releasably sealed to each other isolating the adhesive layer from the surroundings, and where the cover layer is releasably fastened to the top layer.

15 Claims, 3 Drawing Sheets

LAYERED PRODUCT READY FOR NON TOUCH APPLICATION AND A METHOD FOR PRODUCING SUCH A PRODUCT

FIELD OF THE INVENTION

The present invention relates to a layered product in a package ready for non-touch application which product comprises a cover layer to which an adhesive layer is unreleasably fastened and a release layer which is releasably fastened to the adhesive layer. The package comprises a top layer and a bottom layer where the top layer is next to the cover layer and the bottom layer is next to the adhesive layer and the top and bottom layers are releasably sealed to each other isolating the adhesive layer from the surroundings.

BACKGROUND OF THE INVENTION

It is desirable to be able to apply an adhesive product such as a dressing without touching the adhesive layer in order to avoid reducing the adhesiveness of the product. Also it is desirable to be able to apply a sterile dressing to a patient's skin without touching the surface of the dressing that is to come into contact with the skin in order to avoid introducing bacteria to the wound.

The prior art discloses several methods for facilitating handling of wound dressings and one method is described in U.S. Pat. No. 5,106,629 (NDM Acquisition Corp.). The product of this patent is constituted of three layers: a dimensionally stable backing layer, a transparent adhesive layer and a release layer. When applying the dressing, the release layer is removed by using an extending tab attached thereto, to expose the adhesive layer. The remaining layers of the wound dressing are then applied to the wound site with the adhesive layer directly contacting the wound. Once these layers are in place, the dimensionally stable backing member is removed, preferably using an extending tab attached hereto.

Another method is described in WO 97/43991 (Coloplast A/S). The object of this invention is to ensure easy handling of a wound dressing which comprises a main part and a handle part. The main part comprises a carrier layer, an adhesive layer and a release liner. The handle part comprises one or more tab members designed for use as a "non-touch" grip when applying the dressing to the skin. The tab member and the main part of the dressing do not have all layers in common, reducing the force which needs to be applied in order to remove the tab member after applying the dressing.

These two documents explain how to handle the product without touching the adhesive during application but they do not combine discrete packaging of the products with non-touch application of the products.

A third product—a medical adhesive composite—is described in WO 98/00080 (Minnesota Mining and Manufacturing Company). This medical adhesive composite, e.g. a dressing, is combined with a package, the packaged product comprises a top sheet of packaging material, a carrier material, a conformable backing material, a pressure sensitive adhesive and a bottom sheet of packaging material with a release surface. The carrier material is preferably substantially more rigid than the backing material in order to prevent the backing from wrinkling or folding onto itself in whole or in part during application of the dressing. The carrier material is capable of being attached to the backing by any suitable method, such as heat sealing, adhesives, mechanical bonds, wax coatings etc. The bond is secure, yet releasable, i.e. the carrier and backing can be separated without destroying the integrity of the backing or the bond between the adhesive on the backing and the skin of a patient. In addition the bond between the carrier and the backing should be stronger than the bond between the adhesive on the bottom face of the backing and the release liner or surface of the packaging. Adhering the medical adhesive composites directly to the bottom sheet of the packaging material rather than including a separate release liner on the product simplifies the process of dispensing the medical adhesive composites. The bond strength between the release surface and the bottom sheet is greater than the bond strength between the release surface and the adhesive on the bottom face of the backing.

This document shows how it is possible to include packaging of the product into a single process but the used process is rather complicated and the packaged product may be difficult to apply.

In EP Patent Application No. 938 882 is disclosed a release paper in the form of a sheet with several discrete plasters. The plasters comprise an adhesive layer, covered on one side with the release paper and on the other side with a top film. A pouch covering the wound area maybe located between the adhesive and the release paper. The plasters are separated from each other by a perforated line in the release paper. The product is not in the form of a sealed package as it does not comprise a sealing cover layer on top of the construction.

BRIEF DESCRIPTION OF THE INVENTION

The object of the invention is to provide a product in a discrete package which product is easy to handle without the user touching the adhesive of the product which will be touching the surface to which the product is applied, and at the same time this product is easier and less expensive to produce.

This object is achieved by fastening the cover layer releasably to the top layer of the package in order to make it possible to use the top layer as a non-touch grip.

A carrier layer is a coherent web which is used to move the layered product through the production process even after other layers have been cut into their final size and it reduces the cost of production when the carrier layer is made a part of the finished product instead of wasting the carrier layer totally or partly during the production process.

In order to make the process very simple, the top layer may be the carrier layer but it is also possible to use a second layer as carrier layer and, in this case, the second layer may be present between the cover layer and the top layer in the finished product. In this case the bond strength R1 between the cover layer and the second layer is smaller than the bond strength S1 between the second layer and the top layer. In fact S1 may be so large it is considered unreleasable.

It is possible to add a release layer as a separate layer and use standard material for the process; otherwise the release layer can be a release surface on the upper side of the bottom layer of the package.

In order to make the application procedure as simple as possible for the user of the product it is advantageous that:
1) the bond strength R1 between the top layer of the package or a second layer and the cover layer is higher than the bond strength R2 between the adhesive layer and the release layer, and
2) the bond strength R4 between the release layer and the bottom layer of the package is higher than the bond strength R2 between the adhesive layer and the release layer, and 3) the bond strength between the adhesive layer and the surface to which the product has been applied is higher than the bond strength R1.

When the user applies a dressing which agrees with the above demands for the bond strength between the different layers, the user first separates the top layer and the bottom layer of the package. When doing this, the release layer—whether this layer is a part of the bottom layer or a separate layer—will come off together with the bottom layer and afterwards the bottom layer and the release layer can be thrown away. This leaves the user with the top layer to which the product comprising the cover layer and an adhesive layer is attached. Now the user can use the top layer of the package to handle the product and assure the product is placed correctly. When the adhesion between the layered product and the surface to which the product is fastened is higher than the bond strength between the top layer and the cover layer, the user can remove the top layer of the package from the applicated product without problems and throw it away.

DETAILED DESCRIPTION OF THE INVENTION

Figure 1:
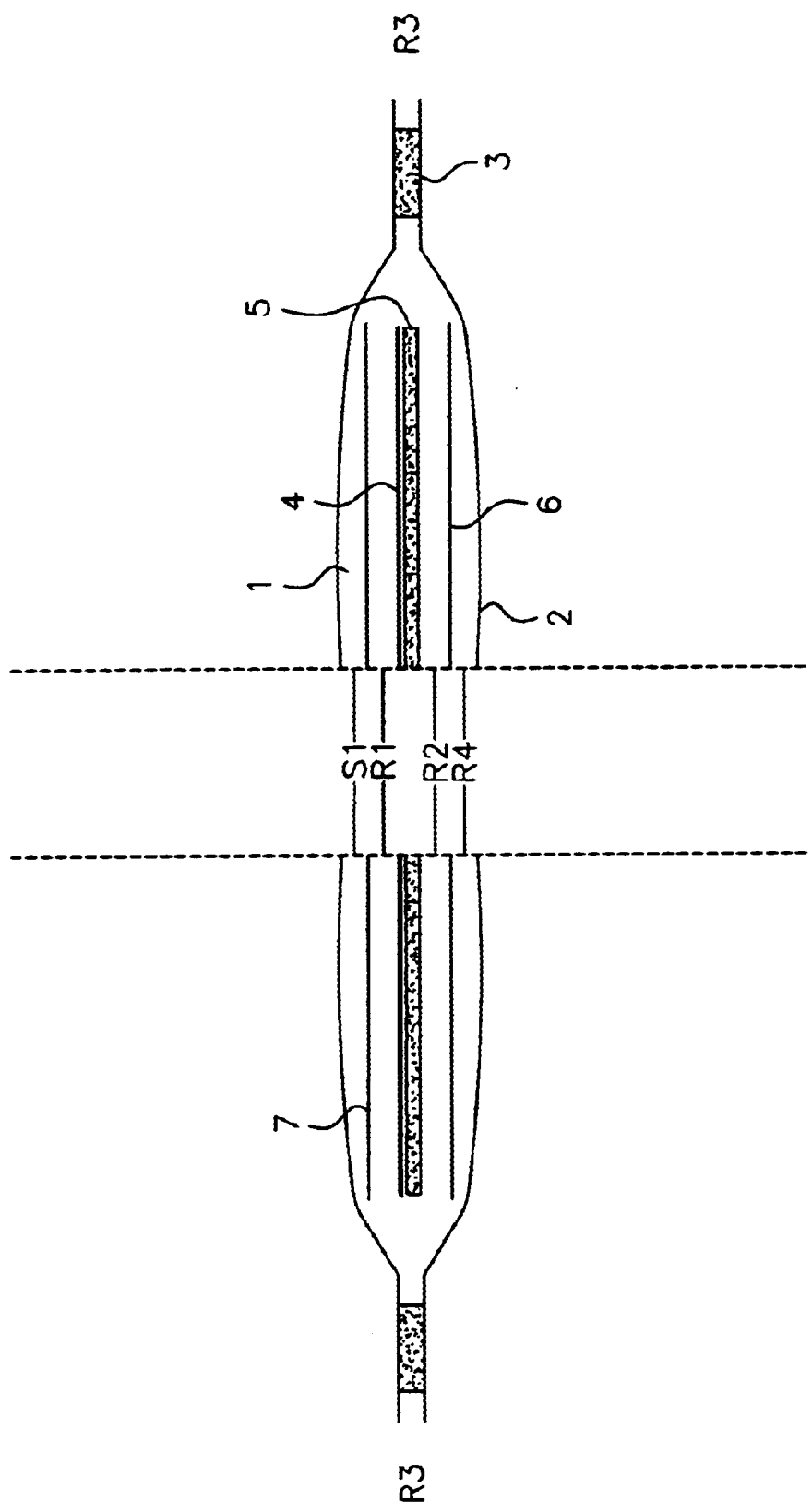
FIG. 1 shows a cross-sectional view of a product and a package according to the present invention.

FIG. 1 shows a cross-sectional view of a product and a package. The package is constituted by two outer layers, namely a top layer 1 and a bottom layer 2. These two layers are sealed together at 3 in a way that completely isolates the product from the surroundings, and the sealing represents a bond strength of R3.

A cover layer 4 is placed below the top layer and these two layers are releasably fastened to each other with the bond strength R1. The function of the cover layer 4 is to establish a non-adhesive and comfortable upper side of the product when the product is in use. When the product is a dressing, the cover layer can be woven or non-woven, e.g., a polymeric material such as a polyurethane with a certain permeativity for water. It is also possible to place a separate layer such as a carrier layer 7 between the top layer and the cover layer and then the bond strength S1 between the top layer and the optional carrier layer 7 can suitably be considerably higher than the bond strength R1 between the cover layer and the carrier layer.

Below the cover layer 4 is an adhesive layer 5. The cover layer 4 and the adhesive layer 5 are unreleasably bonded to each other. By "unreleasably bonded" it is understood that it is not possible to separate the two layers and keep them both intact and, according to this definition of "unreleasably", the two layers may consist of one layer with different surface structure on the upper and lower sides. If the product is a dressing, the adhesive may contain hydrocolloids.

The adhesive layer 5 is protected by a release surface. In FIG. 1 the release surface is constituted by a separate layer, a release layer 6, but the release surface may also be a part of the surface of the bottom layer having releasing qualities. The bond strength between the adhesive layer 5 and the release surface is R2. The bond strength between an optional separate release layer 6 and the bottom layer 2 is R4.

Figure 2:
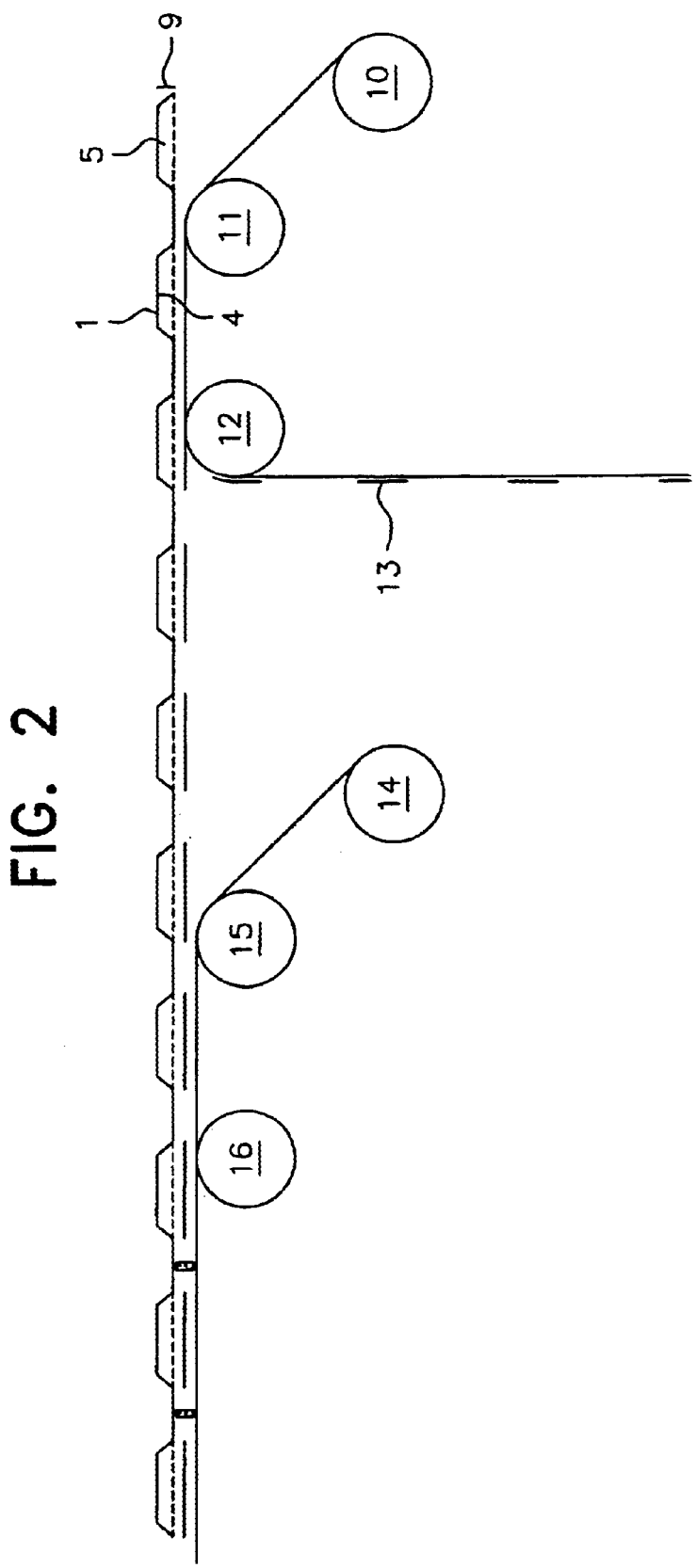
FIG. 2 is a schematic diagram of a continuous method of manufacturing a product according to the present invention.

FIG. 2 shows a schematic diagram of a continuous process which may be used for manufacturing the product of this invention. The primary layered web 9 that enters the process comprises a carrier layer which in this example is the later top layer 1 of the package, a cover layer 4 which will form a non-adhesive surface of the applicated product and a layer of or discrete portions of adhesive 5 which has/have been fastened unreleasably to the cover layer 4.

A roll 10 contains a supply of release liner and the release liner is attached to the primary layered web 9 at the roll 11. Hereafter the primary web 9 to which the release liner now is attached passes a station 12 where the layers of the web which constitute the product, the cover layer 4, the adhesive layer 5 and the release layer 6, are cut into desired discrete products. The weed 13 from this action is removed and only the carrier layer—the top layer 1 of the package—still constitutes a coherent layer.

When the weed 13 has been removed it is time to add the bottom layer of the package to the line of products. A supply roll of the bottom layer is kept at 14 and the bottom layer is attached to the line of products at the station 15.

After the bottom layer of the package has been attached to the line of products, the individual products have to be isolated. This is done at the station 16 where the top and the bottom layers of the package are fastened releasably to each other by, e.g., peel welding.

It is also possible to apply a more batchwise process for manufacturing of the products. This is especially advantageous if the process producing the web 9 is very fast and it is difficult for a single packaging machine to keep up.

Figure 3:
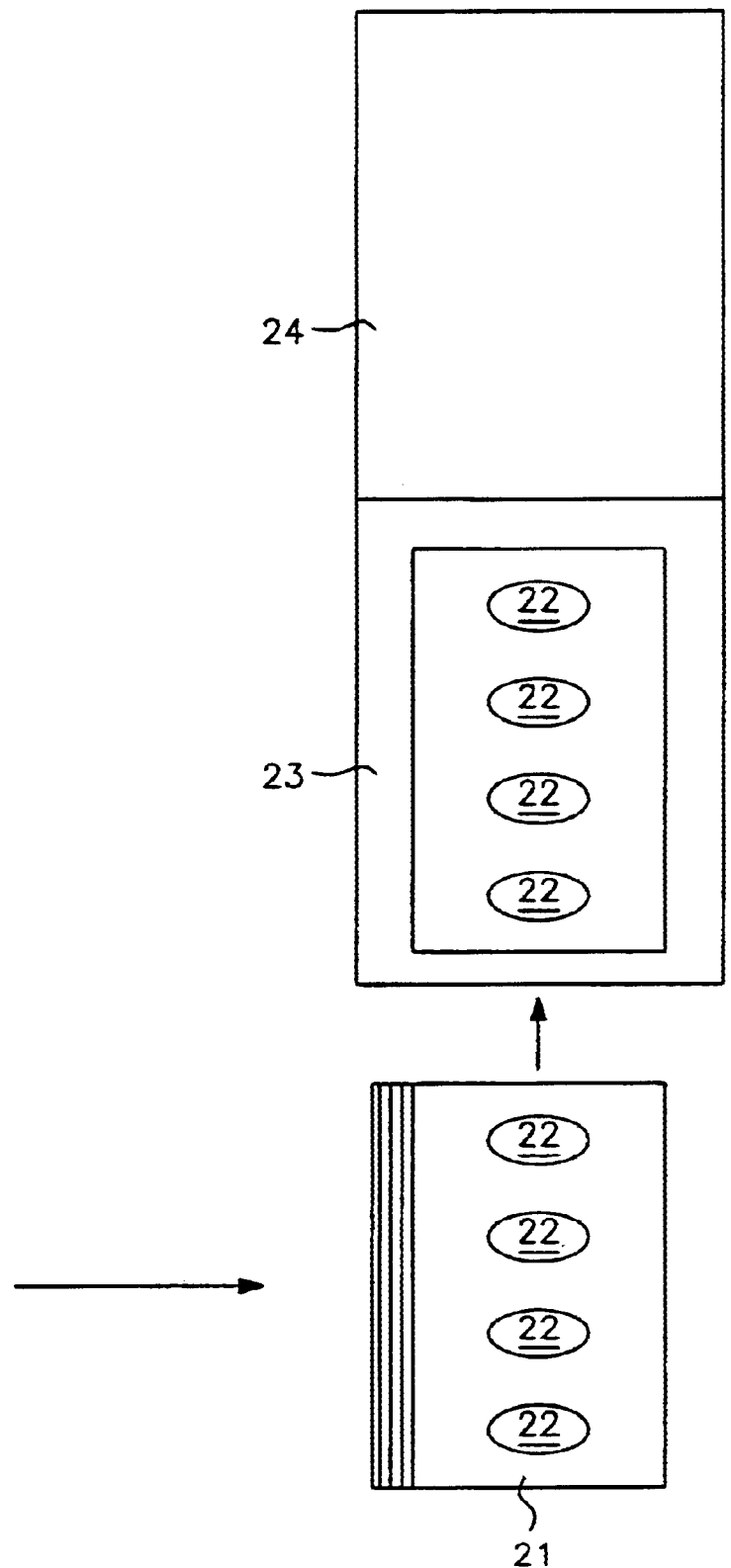
FIG. 3 is a schematic diagram of a batchwise method of manufacturing a product according to the present invention.

After the products have passed the roll 12 of FIG. 2 where the line of products have been die cut, the endless line of products is cut up into units containing several discrete products 22 (in FIG. 3 the units contain four discrete products). The units are then collected and moved to a temporary storage or directly to one or more different packing machines. In order to be able to pile the units for storage or transport the units have to be provided with a release liner.

In FIG. 3 is a schematic diagram of a batchwise process where the units consisting of discrete products 22 arrive at the packing machines in piles 21. The top unit is moved forward and placed on the bottom layer 23 of the package, to which layer the release-liner covered surface of the product is fastened with the bond strength R4 by, e.g., gluing or peel welding.

In this process the bottom layer 23 and the top layer 24 of the package are constituted by a single sheet of package material. After placing and fastening the unit on the bottom layer, the top layer is folded over the unit and fastened to the bottom layer by the bond strength R3 and to the cover layer of the products by the bond strength R1, e.g., in such a way that the products are isolated as discrete products.

What is claimed is:

1. A layered product in a package at ready for non-touch application comprising:
    a cover layer having an upper surface and a lower surface to which an adhesive layer is unreleasably fastened;
    a release layer which is releasably fastened to the adhesive layer; and
    a top layer and a bottom layer where the top layer is next to the cover layer and the bottom layer is next to the release layer, said top and bottom layers being releasably sealed to each other isolating the adhesive layer from the surroundings, said upper surface of said cover layer being releasably fastened directly to the top layer.

2. The layered product in a package ready for non-touch application according to claim 1 wherein a carrier layer forms a part of the packaged product.

3. The layered product in a package ready for non-touch application according to claim 2 wherein the top layer is also the carrier layer.

4. The layered product in a package ready for non-touch application according to claim 1 wherein:
1) a bond strength R1 between the top layer of the package and the cover layer is higher than a bond strength R2 between the adhesive layer and the release layer;
2) a bond strength R4 between the release layer and the bottom layer of the package is higher than the bond strength R2 between the adhesive layer and the release layer; and
3) a bond strength between the adhesive layer and the surface to which the product has been applied is higher than the bond strength R1.

5. A method for producing a layered product in a package having a top layer and a bottom layer ready for non-touch application comprising the steps of:
a) providing a web having at least three layers including a carrier layer connected to or constituting the top layer of a package, a cover layer and an adhesive layer, said cover layer and said adhesive layer being unreleasably fastened to each other;
b) die cutting the product into discrete portions still attached to the carrier layer;
c) attaching the bottom layer to the adhesive side of the product; and
d) isolating the product by sealing the top layer to the bottom layer in a way that completely isolates the product from the surroundings.

6. A method for producing a layered product in a package having a top layer and a bottom layer ready for non-touch application comprising the steps of:
a) providing a web having at least three layers including a carrier layer connected to or constituting the top layer of a package, a cover layer and an adhesive layer, said cover layer and said adhesive layer being unreleasably fastened to each other;
b) attaching a release layer to said adhesive layer;
c) die cutting the product into discrete portions still attached to the carrier layer;
d) attaching the bottom layer to said adhesive layer; and
e) sealing the top layer to the bottom layer in a way that completely isolates the product from the surroundings.

7. A method for applying a layered product packed in a package and prepared for non-touch application comprising the steps of:
1) providing a top layer and a bottom layer of the package that are bonded to each other by a bond strength R3, with a cover layer of the layered product being fastened to the top layer by a bond strength R1 and an adhesive layer of said layered product being fastened to a release layer by a bond strength R2, the bond strength R1 being greater than R2 so the layered product will stay fastened to the top layer;
2) separating the top and the bottom layers;
3) removing the bottom layer and the release layer;
4) adhering the layered product on the surface to which the product needs to be applied, a bond strength between said surface and the layered product being higher than the bond strength R1; and
5) removing the top layer.

8. A layered product in a package ready for non-touch application comprising:
a cover layer having an upper surface and a lower surface to which an adhesive layer is unreleasably fastened;
a release surface which is releasably fastened to the adhesive layer;
a top layer and a bottom layer releasably sealed to each other to enclose and isolate the cover layer and adhesive layer from the surroundings, said bottom layer being next to the adhesive layer; and
a carrier layer between the top layer and the upper surface of the cover layer, said carrier layer being fastened to said top layer and releasably fastened to said upper surface of said cover layer.

9. The layered product in a package ready for non-touch application according to claim 8 wherein the release surface is integral with said bottom layer.

10. The layered product in a package ready for non-touch application according to claim 8 wherein a separate release layer is present between the adhesive layer and the bottom layer, said release layer having said release surface thereon.

11. The layered product in a package ready for non-touch application according to claim 10 wherein:
1) a bond strength R1 between the carrier layer and the cover layer is higher than a bond strength R2 between the adhesive layer and the release layer;
2) a bond strength R4 between the release layer and the bottom layer of the package is higher than the bond strength R2 between the adhesive layer and the release layer; and
3) a bond strength between the adhesive layer and the surface to which the product has been applied is higher than the bond strength R1.

12. The layered product in a package ready for non-touch application according to claim 8 wherein a bond strength R1 between the carrier layer and said cover layer is smaller than a bond strength S1 between said carrier layer and said top layer.

13. A layered product in a package ready for non-touch application comprising:
a cover layer to which an adhesive layer is unreleasably fastened;
a release layer which is releasably fastened to the adhesive layer with a bond strength R2;
a top layer and a bottom layer releasably sealed to each other so as to enclose and isolate the cover layer and the adhesive layer from the surroundings, the bottom layer being next to the release layer, and the top layer being releasably fastened to the cover layer with a bond strength R1 that is greater than the bond strength R2.

14. The layered product in a package ready for non-touch application according to claim 13 further comprising a carrier layer present between and fastened to said cover layer and said top layer.

15. The layered product in a package ready for non-touch application according to claim 14 wherein said cover layer is fastened to said carrier layer with the bond strength R1 and said top layer is fastened to said carrier layer with a bond strength S1 that is larger than the bond strength R1.

* * * * *